United States Patent
Reiley

(10) Patent No.: US 9,585,760 B2
(45) Date of Patent: *Mar. 7, 2017

(54) FACET ARTHOPLASTY DEVICES AND METHODS

(71) Applicant: GLOBUS MEDICAL, INC., Audubon, PA (US)

(72) Inventor: Mark A. Reiley, San Jose, CA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/795,934

(22) Filed: Jul. 10, 2015

(65) Prior Publication Data

US 2015/0374506 A1  Dec. 31, 2015

Related U.S. Application Data

(60) Continuation of application No. 13/740,947, filed on Jan. 14, 2013, now Pat. No. 9,107,759, which is a
(Continued)

(51) Int. Cl.
| | |
|---|---|
| *A61B 17/88* | (2006.01) |
| *A61F 2/44* | (2006.01) |
| *A61B 17/16* | (2006.01) |
| *A61B 17/86* | (2006.01) |
| *A61F 2/28* | (2006.01) |

(Continued)

(52) U.S. Cl.
CPC ........ *A61F 2/4405* (2013.01); *A61B 17/1671* (2013.01); *A61B 17/86* (2013.01); *A61F 2/28* (2013.01); *A61F 2002/305* (2013.01); *A61F 2002/30387* (2013.01); *A61F 2002/30433* (2013.01); *A61F 2002/30537* (2013.01); *A61F 2002/30604* (2013.01); *A61F 2002/30777* (2013.01); *A61F 2002/30874* (2013.01); *A61F 2002/449* (2013.01); *A61F 2002/4631* (2013.01); *A61F 2220/0025* (2013.01); *A61F 2220/0041* (2013.01); *A61F 2250/0004* (2013.01); *A61F 2310/00017* (2013.01); *A61F 2310/00023* (2013.01); *A61F 2310/00029* (2013.01); *A61F 2310/0097* (2013.01); *A61F 2310/00131* (2013.01); *A61F 2310/00179* (2013.01); *A61F 2310/00329* (2013.01); *A61F 2310/00604* (2013.01); *A61F 2310/00634* (2013.01); *A61F 2310/00976* (2013.01)

(58) Field of Classification Search
CPC ............ A61B 17/7064; A61B 17/7067; A61B 17/1757; A61B 17/1671; A61B 2017/0256
USPC .............................. 606/246–279, 70, 71, 282
See application file for complete search history.

(56) References Cited

U.S. PATENT DOCUMENTS

| | | | | |
|---|---|---|---|---|
| 4,567,337 A | * | 1/1986 | Woods, I | H01H 23/141 200/331 |
| 6,238,396 B1 | * | 5/2001 | Lombardo | A61B 17/7052 606/251 |

* cited by examiner

*Primary Examiner* — Mary Hoffman
*Assistant Examiner* — Tara R Carter

(57) ABSTRACT

Surgically installed prostheses replace either the caudal portion of a natural facet joint, the cephalad portion of a natural facet joint, or both. The prostheses are readily attached to the pedicles of a vertebral body and support at least one element that defines an artificial facet joint structure. The caudal facet joint structure is sized and located to articulate with the cephalad facet joint structure. Together, the prostheses form a total facet replacement system. The system is suitable for use in virtually all levels of the spine.

16 Claims, 6 Drawing Sheets

Related U.S. Application Data continuation of application No. 12/806,410, filed on Aug. 12, 2010, now Pat. No. 8,377,103, which is a continuation of application No. 11/957,149, filed on Dec. 14, 2007, now abandoned, which is a continuation of application No. 10/961,726, filed on Oct. 8, 2004, now abandoned, which is a division of application No. 10/067,137, filed on Feb. 4, 2002, now Pat. No. 6,811,567, which is a continuation-in-part of application No. 09/693,272, filed on Oct. 20, 2000, now Pat. No. 6,610,091.

(60) Provisional application No. 60/160,891, filed on Oct. 22, 1999.

(51) Int. Cl.
*A61F 2/30* (2006.01)
*A61F 2/46* (2006.01)

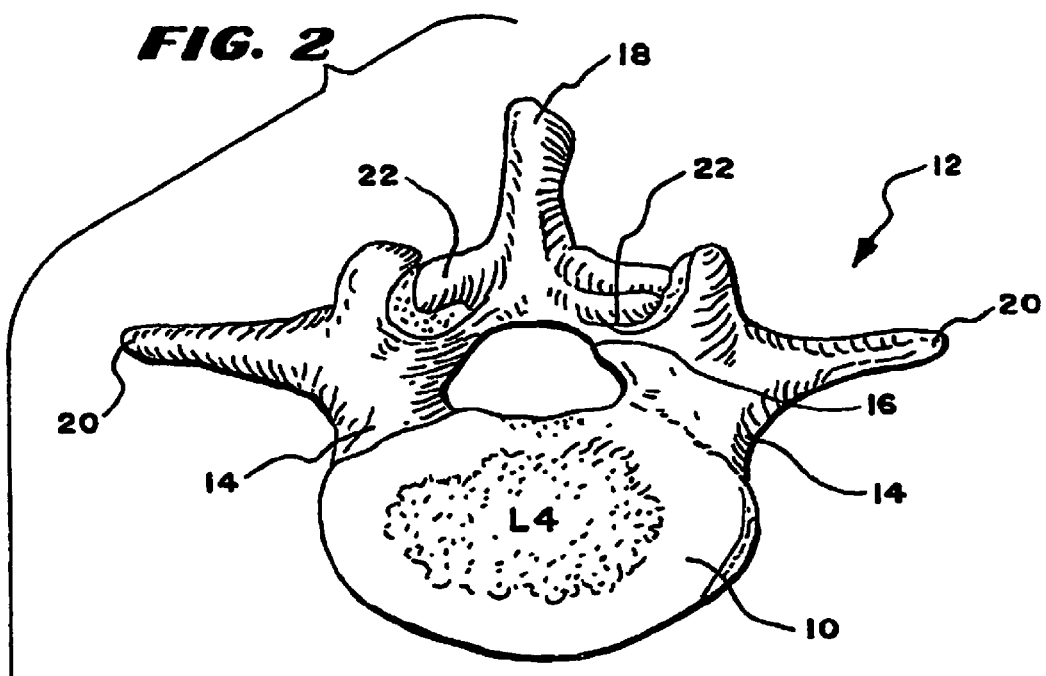
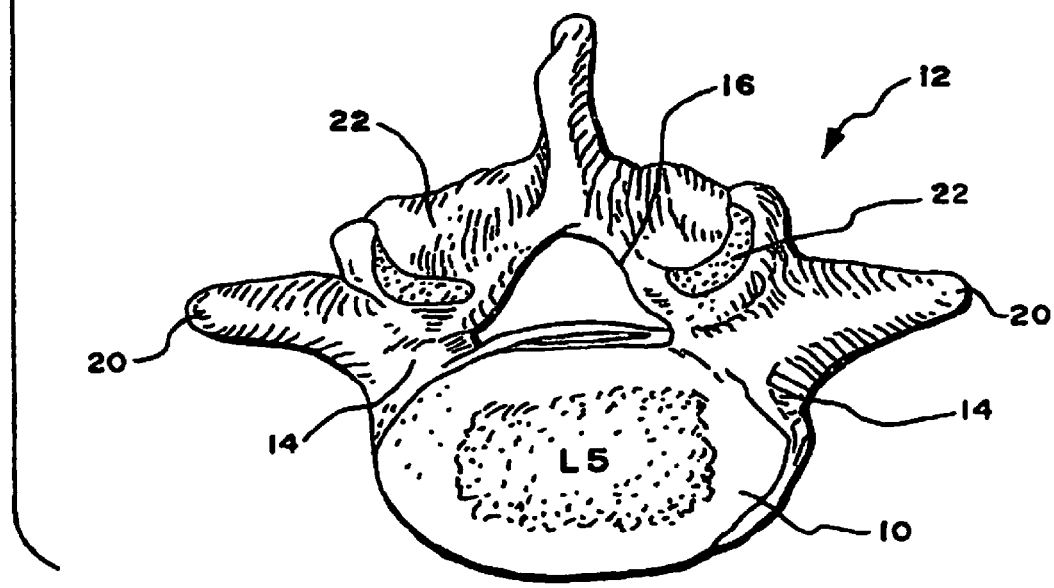
FIG. 2

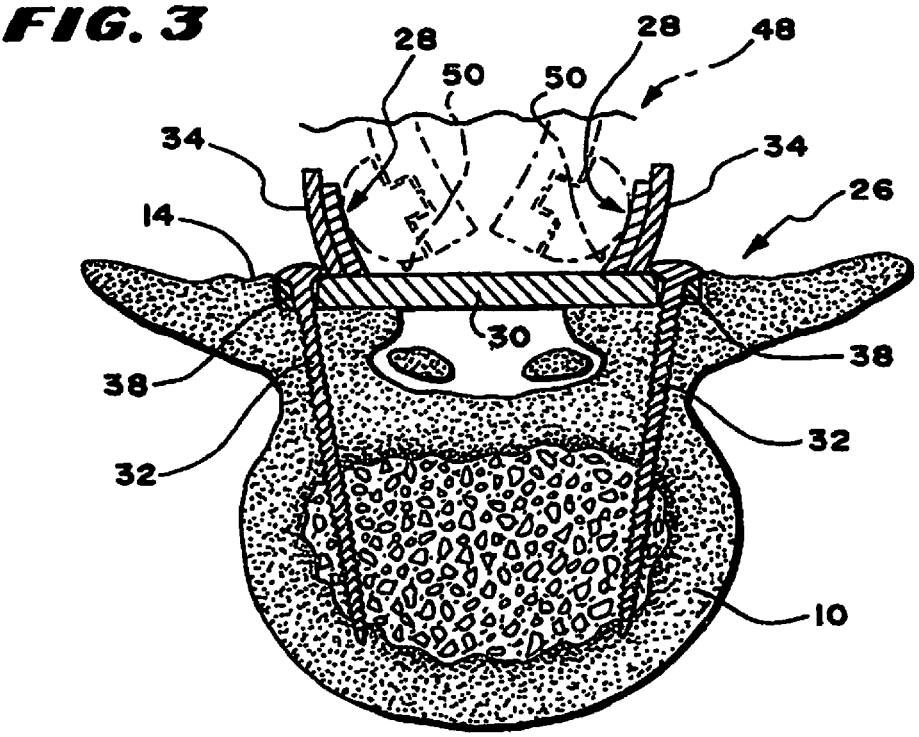
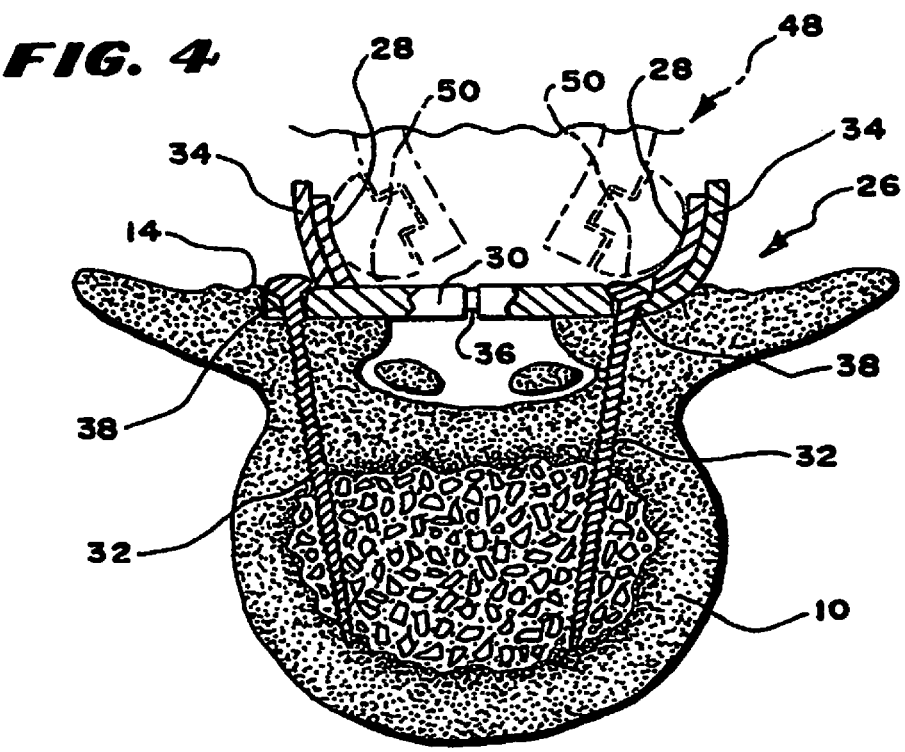

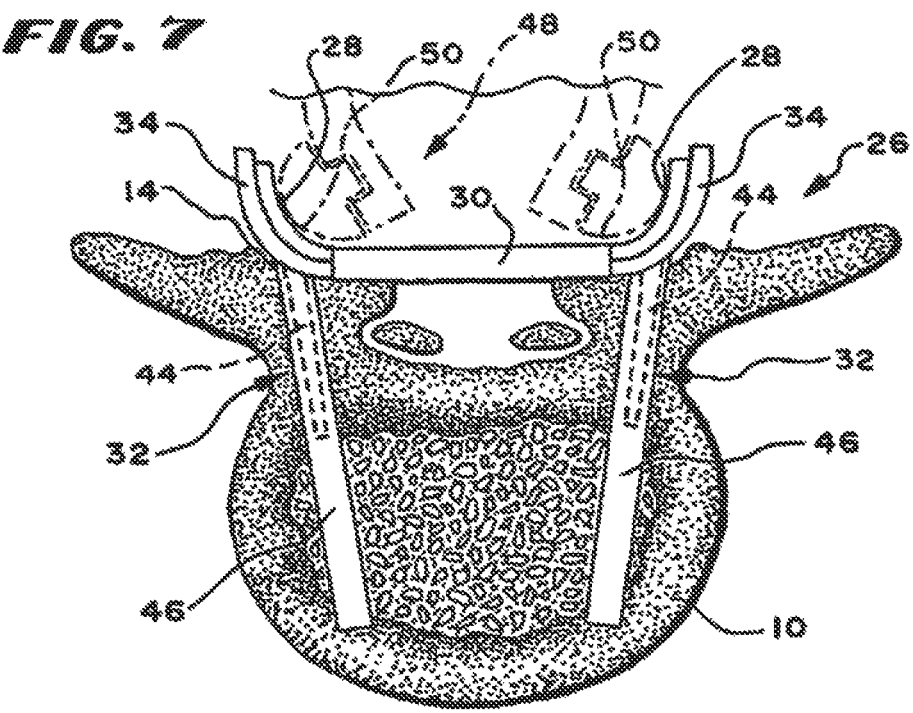
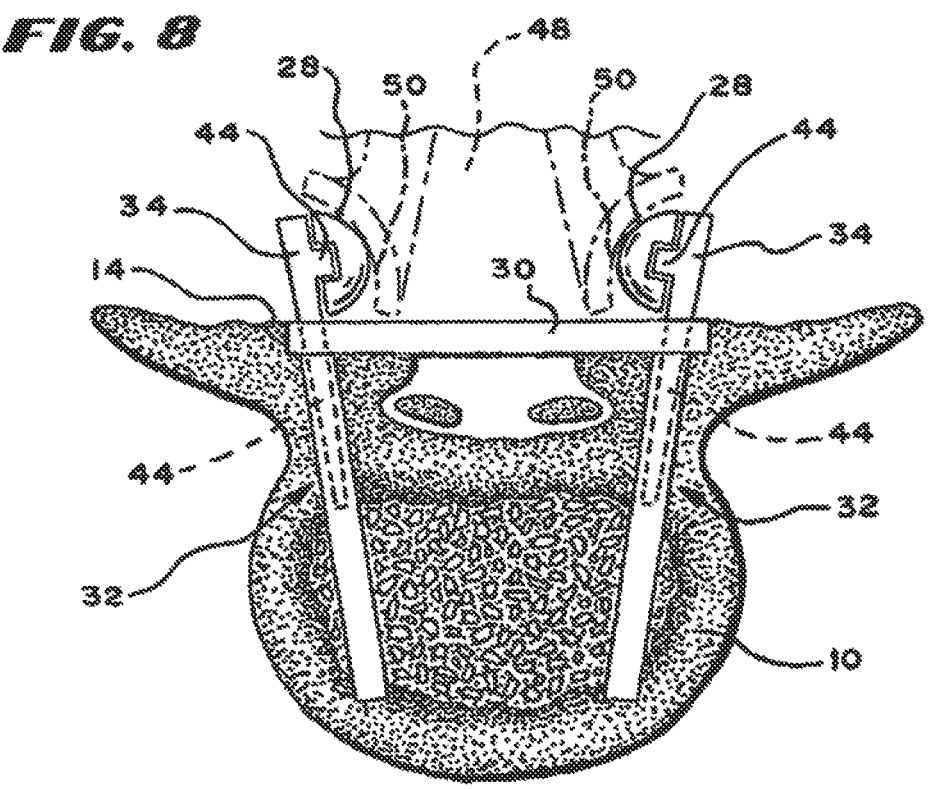

FACET ARTHOPLASTY DEVICES AND METHODS

CROSS REFERENCE TO RELATED APPLICATIONS

This application is a continuation application of U.S. patent application Ser. No. 13/740,947, filed Jan. 14, 2013, which is a continuation of U.S. patent application Ser. No. 12/806,410, filed on Aug. 12, 2010, now issued as U.S. Pat. No. 8,377,103, which is a continuation of U.S. patent application Ser. No. 11/957,149, filed Dec. 14, 2007, which is a continuation of U.S. patent application Ser. No. 10/961,726, filed Oct. 8, 2004, which is a divisional of U.S. patent application Ser. No. 10/067,137, filed Feb. 4, 2002, now U.S. Pat. No. 6,811,567, which is a continuation-in-part of U.S. patent application Ser. No. 09/693,272, filed Oct. 20, 2000, now U.S. Pat. No. 6,610,091, which claims the benefit of Provisional Patent Application Ser. No. 60/160,891, filed Oct. 22, 1999, all of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention generally relates to devices and surgical methods for the treatment of various types of spinal pathologies, More specifically, the present invention is directed to several different types of facet joint replacement prostheses, surgical procedures for performing facet joint replacements, and surgical instruments which may be used to perform the surgical procedures.

BACKGROUND OF THE INVENTION

Back pain is a common human ailment. In fact, approximately 50% of persons who are over 60 years old suffer from lower back pain. Although many incidences of back pain are due to sprains or muscle strains which tend to be self-limited, some back pain is the result of more chronic fibromuscular, osteoarthritic, or ankylosing spondolytic processes of the lumbosacral area. Particularly in the population of over 50 year olds, and most commonly in women, degenerative spine diseases such as degenerative spondylolisthesis (during which one vertebra slides forward over the top of another vertebra) and spinal stenosis (during which the spinal canal markedly narrows) occurs in a high percentage of the population. Iida, et al, 1989.

Degenerative changes of the adult spine have traditionally been determined to be the result of the interrelationship of the three joint complex: the disk and the two facet joints. Degenerative changes in the disc lead to arthritic changes in the facet joint and vice versa. See Farfan and Sullivan, 1967; see also Farfan, 1969; see also Farfan, 1980.

One cadaver study of nineteen cadavers with degenerative spondylolisthesis showed that facet degeneration was more advanced than disc degeneration in all but two cases. Farfan. In mild spondylolisthetic cases, the slip appeared to be primarily the result of predominantly unilateral facet subluxation. Other studies into degenerative changes of the spine have revealed extensive contribution of facet joint degeneration to degenerative spinal pathologies such as degenerative spondylolisthesis, central and lateral stenosis, degenerative scoliosis (i.e., curvature of the spine to one side), and kypho-scoliosis, at all levels of the lumbar spine. See Kirkaldy-Willis et al, 1978; see also Rosenberg, 1975.

It has been determined that facet joint degeneration particularly contributes to degenerative spinal pathologies in levels of the lumbar spine with sagittally oriented facet joints, i.e. the L4-L5 level.

When intractable pain or other neurologic involvement results from adult degenerative spine diseases, such as the ones described above, surgical procedures may become necessary. Traditionally, the surgical management of disease such as spinal stenosis consisted of decompressive laminectomy alone. Herkowitz, et al, The Diagnosis and Management of Degenerative Lumber Spondylolisthesis, 1998. Wide decompressive laminectomies remove the entire lamina, and the marginal osteophytes around the facet joint. Because a lot of degenerative spine disease has been demonstrated to be caused by facet joint degeneration or disease, this procedure removes unnecessary bone from the lamina and insufficient bone from the facet joint.

Furthermore, although patients with one or two levels of spinal stenosis tend to do reasonably well with just a one to two level wide decompressive laminectomy, patients whose spinal stenosis is associated with degenerative spondylolisthesis have not seen good results. Lombardi, 1985. Some studies reported a 65% increase in degree of spondylolisthesis in patients treated with wide decompressive laminectomy. See Johnson et al; see also White and Wiltse. The increase in spinal slippage especially increased in patients treated with three or more levels of decompression, particularly in patients with radical laminectomies where all of the facet joints were removed.

To reduce the occurrence of increased spondylolisthesis resulting from decompressive laminectomy, surgeons have been combining laminectomies, particularly in patients with three or more levels of decompression, with multi-level arthrodesis, which surgically fuses the facet joints to eliminate motion between adjacent vertebrae. Although patients who undergo concomitant arthrodesis do demonstrate a significantly better outcome with less chance of further vertebral slippage after laminectomy, arthrodesis poses problems of its own. Aside from the occurrence of further spondylolisthesis in some patients, additional effects include non-unions, slow rate of fusion even with autografts, and significant morbidity at the graft donor site. Furthermore, even if the fusion is successful, joint motion is totally eliminated at the fusion site, creating additional stress on healthy segments of the spine which can lead to disc degeneration, herniation, instability spondylolysis, and facet joint arthritis in the healthy segments.

An alternative to spinal fusion has been the use of an invertebral disc prosthesis. There are at least 56 artificial disc designs which have been patented or identified as being investigated. McMillin C. R. and Steffee A. D., 20th Annual Meeting of the Society for Biomaterials (abstract)(1994). Although different designs achieve different levels of success with patients, disc replacement mainly helps patients with injured or diseased discs; disc replacement does not address spine pathologies such as spondylolisthesis and spinal stenosis caused by facet joint degeneration or disease.

SUMMARY OF THE INVENTION

There is a need in the field for prostheses and prosthetic systems to replace injured and/or diseased facet joints, which cause, or are a result of, various spinal diseases. There is also a need for surgical methods to install such prostheses. There is also a need for prostheses and prosthetic systems to replace spinal fusion procedures.

The present invention overcomes the problems and disadvantages associated with current strategies and designs in various treatments for adult spine diseases. The present inventive spinal arthroplastic systems avoid the problems of spine stiffness, increased loads on unfused levels, and predictable failure rates associated with spinal arthrodesis. The present invention pertains to spinal prostheses designed to replace facet joints and/or part of the lamina at virtually all spinal levels including L1-L2, L2-L3, L3-L4, L4-L5, L5-S-1, T11-T12, and T12-L1. Various types of joint replacement prostheses are described for treating different types of spinal problems.

As will be described in greater detail later, a given natural facet joint has a superior half and an inferior half. In anatomical terms, the superior half of the joint is formed by the vertebral level below the joint (which can thus be called the caudal portion of the facet joint, i.e., because it is near the feet). The inferior half of the joint is formed by the vertebral level above the joint (which can thus be called the cephalad portion of the facet joint, i.e., because it is near the head). For example, in the L4-L5 facet joint, the caudal portion of the joint is formed by boney structure on the L-5 vertebra (e.g., a superior articular suface and supporting bone on the L-5 vertebra), and the cephalad portion of the joint is formed by boney structure on the L-4 vertebra (e.g., an inferior articular surface and supporting bone on the L-4 vertebra).

For the sake of description, the prostheses that embody the features of the invention will be called either "cephalad" or "caudad" with relation to the portion of a given facet joint they replace. Thus, a prosthesis that, in use, replaces the caudal portion of a facet joint (i.e., the superior half) will be called a "caudal" prosthesis. Likewise, a prosthesis that, in use, replaces the cephalad portion of a facet joint (i.e., the inferior half) will be called a "cephalad" prosthesis.

One aspect of the invention provides a facet joint prosthesis to replace, on a vertebral body, a caudal portion of a natural facet joint (e.g., a superior articular surface and supporting bone structure on the vertebral body). The caudal prosthesis comprises a component sized to be fixed to the vertebral body, e.g., on or near a pedicle. The caudal prosthesis includes an artificial facet joint structure adapted to replace a caudal portion of the natural facet joint after its removal from the vertebral body. The removal of a caudal portion of the natural facet joint and its total replacement by the artificial facet joint structure of the caudal prosthesis frees the orientation of the prosthesis from anatomic constraints imposed by a preexisting articular configuration of the caudal portion of the natural facet joint. Furthermore, the artificial facet joint structure of the caudal prosthesis can comprise an artificial articular configuration that is unlike the preexisting articular configuration, so that a desired articulation or bony anatomy can be restored to achieve a desired level of function.

This aspect of the invention also provides a method of replacing, on a vertebral body, a caudal portion of a natural facet joint. The method removes a caudal portion of the natural facet joint from the vertebral body, and, in its place, fixes a component to the vertebral body that includes an artificial facet joint structure adapted to replace the removed caudal portion of the natural facet joint. Desirably, the artificial facet joint structure includes an artificial articular configuration unlike the preexisting articular configuration of the removed caudal portion of the natural facet joint.

Another aspect of the invention provides a facet joint prosthesis to replace, on a vertebral body, a cephalad portion of a natural facet joint (e.g., an inferior articular surface and supporting bone structure on the vertebral body). The cephalad prosthesis comprises a component sized to be fixed to the vertebral body, e.g., on or near a pedicle, or on or near a lamina, or on or near a spinous process, or combinations thereof. The cephalad prosthesis includes an artificial facet joint structure adapted to replace a cephalad portion of the natural facet joint after its removal from the vertebral body. As with the removal and total replacement of a caudal portion of the natural facet joint, the removal of a cephalad portion of the natural facet joint and its total replacement by the artificial facet joint structure of the cephalad prosthesis makes possible the orientation of the prosthesis free from anatomic constraints imposed by a preexisting articular configuration of the cephalad portion of the natural facet joint. Furthermore, like the caudal prosthesis, the artificial facet joint structure of the cephalad prosthesis can comprise an artificial articular configuration that is unlike the preexisting articular configuration of the natural facet surface (which is removed), so that a desired articulation or bony anatomy can be totally restored.

This aspect of the invention also provides a method of replacing, on a vertebral body, a cephalad portion of a natural facet joint. The method removes a cephalad portion of the natural facet joint from the vertebral body, and, in its place, fixes a component to the vertebral body that includes an artificial facet joint structure adapted to replace the removed cephalad portion of the natural facet joint. Desirably, the artificial facet joint structure includes an artificial articular configuration unlike the preexisting articular configuration of the removed cephalad portion of the natural facet joint Another aspect of the invention provides a prosthesis assembly and related method for replacing a natural facet joint between adjoining first vertebral body and a second vertebral bodies. The assembly and method utilize a first component sized to be fixed to the first vertebral body, which is superior to the second vertebral body. The first component includes a first artificial facet joint structure adapted to replace a cephalad portion of the natural facet joint on the first vertebral body after removal of the cephalad portion of the natural facet joint from the first vertebral body. The assembly and method also comprise a second component sized to be fixed to the second vertebral body. The second component includes a second artificial facet joint structure adapted to replace the caudad portion of the natural facet joint of the second vertebral body after removal of the caudad portion of the natural facet joint from the second vertebral body. Together, the first and second artificial facet joint structures comprise an artificial facet joint. The removal of both cephalad and caudal portions of a natural facet joint and their total replacement by the artificial facet joint structures of the first and second components allows the artificial facet joint to be installed without anatomic constraints imposed by a preexisting articular configuration of the natural facet joint. The removal of the natural facet joints also removes bone spurs affecting the nerve roots adjacent the natural facet structures, alleviating or eliminating pain. Furthermore, the artificial facet joint structures of either the first or second components, or both, can create an artificial articular configuration for the artificial facet joint that is unlike the preexisting articular configuration of the removed natural facet joint, so that a desired articulation or bony anatomy can be completely restored. By restoring facet joint articulation to a desired level of function, the incidence of spondylolisthesis can be reduced or eliminated. Other features and advantages of the inventions are set forth in the following Description and Drawings, as well as in the appended claims.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which.

In the drawings:

FIG. 2 is a superior view of the L4 and L5 vertebrae in a separated condition;

FIG. 3 is a superior section view of a vertebral body, showing the fixation of a caudal prosthesis by pedicle screws to a vertebral body, the prosthesis carrying facet joint structure elements that create artificial facet surfaces for the superior half of a facet joint replacement, the artificial facet joint structure elements in FIG. 3 having a generally cup-shaped geometry and being shown in positions medial of the typical anatomic position of the superior half of the facet joint;

FIG. 4 is a superior section view of a vertebral body, showing the fixation of a caudal prosthesis of the type shown in FIG. 3, the length of the prosthesis spanning the pedicles being adjustable, the cup-shaped artificial facet joint structure elements in FIG. 4 being shown in alternative positions either medial or lateral of the typical anatomic position of the superior half of the facet joint;

FIG. 7 is a superior section view of a vertebral body, showing the fixation of a caudal prosthesis by pedicle stems to a vertebral body, the prosthesis carrying facet joint structure elements that create artificial facet surfaces for the superior half of a facet joint replacement, the artificial facet joint structure elements in FIG. 7 having a generally cup-shaped geometry and being shown in positions at or near the typical anatomic position of the superior half of the facet joint;

FIG. 8 is a superior section view of a vertebral body, showing the fixation of a caudal prosthesis of the type shown in FIG. 7, the artificial facet joint structure elements in FIG. 8 having a generally ball-shaped geometry.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE INVENTION

I. Anatomy of Lumbar Vertebrae

Figure 1:
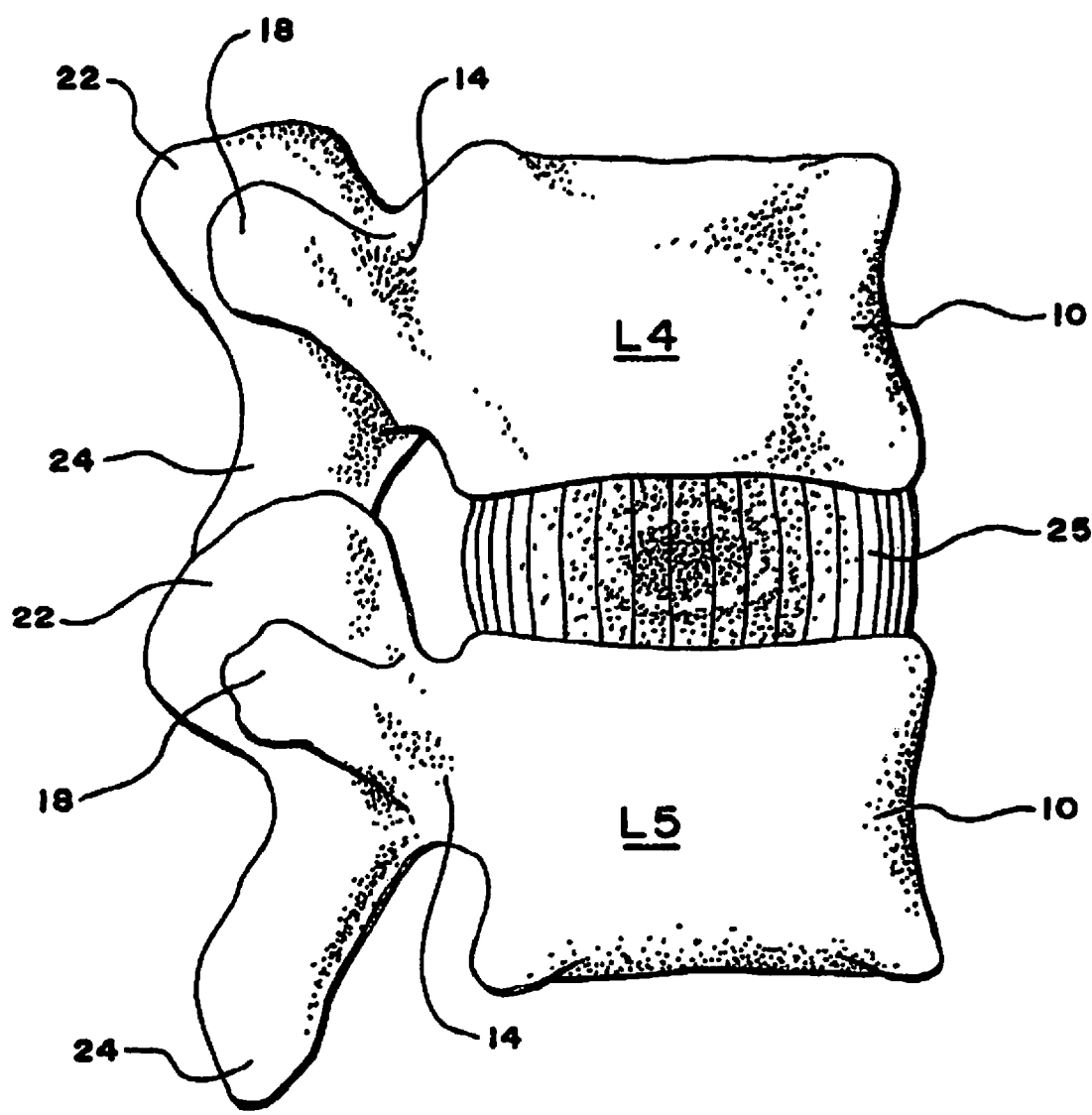
FIG. 1 is a lateral view of the L4 and L5 vertebrae.

FIGS. 1 and 2 show the fourth and fifth lumbar vertebrae L4. and L5, respectively, in a lateral view (while in anatomic association) and in a superior view (separately). The lumbar vertebrae (of which there are a total of five) are in the lower back, also called the "small of the back."

As is typical with vertebrae, the vertebrae L4 and L5 are separated by an intervertebral disk 25. The configuration of the vertebrae L4 and L5 differ somewhat, but each (like vertebrae in general) includes a vertebral body 10, which is the anterior, massive part of bone that gives strength to the vertebral column and supports body weight. The vertebral arch 12 is posterior to the vertebral body 10 and is formed by the right and left pedicles 14 and lamina 16. The pedicles 14 are short, stout processes that join the vertebral arch 12 to the vertebral body 10. The pedicles 14 project posteriorly to meet two broad flat plates of bone, called the lamina 16.

Seven other processes arise from the vertebral arch. Three processes—the spinous process 18 and two transverse 20 processes—project from the vertebral arch 12 and afford attachments for back muscles, forming levers that help the muscles move the vertebrae. The remaining four processes, called articular processes, project superiorly from the vertebral arch (and are thus called the superior articular processes 22) and inferiorly from the vertebral arch (and are thus called the inferior articular processes 24).

The superior and inferior articular processes 22 and 24 are in opposition with corresponding opposite processes of vertebrae superior and inferior adjacent to them, forming joints, called zygapophysial joints or, in short hand, the facet joints or facets. The facet joints permit gliding movement between the vertebrae L4 and L5. Facet joints are found between adjacent superior and inferior articular processes along the spinal column.

The facet joints can deteriorate or otherwise become injured or diseased, causing lack of support for the spinal column, pain, and/or difficulty in movement.

As described in this Specification, a facet joint has a superior half and an inferior half. The superior half of the joint is formed by the vertebral level below the joint (which will accordingly be called the caudal portion of the facet joint), and the inferior half of the joint is formed by the vertebral level above the joint (which will accordingly be called the cephalad portion of the facet joint). For example, in the L4-L5 facet joint, the caudal portion of the facet joint is formed by superior articular surfaces and supporting boney structures on the L-5 vertebra, and the cephalad portion of the facet joint is formed by inferior articular surfaces and supporting boney structures on the L-4 vertebra.

II. Caudal Universal Facet Prosthesis

A. Structure

FIG. 3 shows a caudal facet joint replacement prosthesis 26 that embodies features of the invention. The prosthesis 26 is designated "caudal" because it creates an artificial facet joint structure 28 for the superior half of a facet joint replacement. The caudal prosthesis 26 allows for the removal and replacement of injured, diseased and/or deteriorating natural superior articular surfaces and supporting boney structure on the vertebral body below the facet joint, to provide improved support for the spinal column.

The artificial facet joint structure 28 articulates with the inferior half of the facet joint, which itself can comprise the natural cephalad portions of the facet joint (i.e., inferior articular surfaces and supporting boney structure on the vertebral body above the facet joint), or an artificial facet joint structure formed by a cephalad joint replacement prosthesis 48 (shown in phantom lines in FIG. 3 and as will be described. later).

As will become apparent, the prosthesis 26 is particularly well suited to double-sided procedures and/or for procedures involving vertebral bodies that are not symmetrical.

As shown in FIG. 3, the prosthesis 26 comprises a bar element 30. The bar element 30 is secured to a vertebral body 10 by at least one fixation element 32. As also shown in FIG. 3, the bar element 30 carries at least one facet joint structure element 34. In FIG. 3, two fixation elements 32 (left and right) and two facet joint structure elements 34 (left and right) are shown. The prosthesis 26 thereby readily accommodates a double-sided (i.e., left and right) caudal facet joint replacement.

The bar element 30 is sized and shaped to span the distance between left and right pedicles 14 of a vertebral body 10. The bar element 30 may be formed of a material commonly used in the prosthetic arts including, but not limited to, polyethylene, rubber, titanium, chrome cobalt, surgical steel, bony in-growth sintering, sintered glass, artificial bone, ceramics, or a combination thereof.

As shown in FIG. 3, the spanning length of the bar element 30 may be fixed. Alternatively, as shown in FIG. 4, the spanning length of the bar element 30 may be adjustable by the inclusion of an intermediate sliding joint 36. The adjustment of the spanning length of the bar element 30 may also be made, e.g., by use of a turning gear wheel mechanism, or a ratchet mechanism, or the like. A surgeon thereby has the capability to size the bar element 30, to custom-fit the prosthesis 26 during surgery.

In FIGS. 3 and 4, each end of the bar element includes an opening 38. Each opening 38 accommodates passage of the fixation element 32. In FIG. 1, the fixation elements 32 take the form of pedicle screws or nails. The fixation elements 32 secure the left and right ends of the bar element 30, respectively, to the left and right pedicles 14 of the vertebral body 10.

One or both of the openings 38 could be elongated, either along the superior-inferior axis of the vertebral body, or transverse this axis, to allow for varying orientations and/or sizes of the fixation elements 32. Passage of the fixation elements 32 through openings 38 provides straightforward and flexible fixation of the bar element 30 to the vertebral body 10.

The bar element 30 shown in FIGS. 3 and 4 carries left and right facet joint structure elements 34. The presence of the bar element 30 spanning between the facet joint structure elements 34 lends overall stability to the prosthesis 26. Weight borne by the left and right facet joint structure elements 34 is evenly distributed by the bar element 30 between the left and right sides of the vertebral body 10.

The facet joint structure elements 34 may be fixedly attached to the bar element (e.g., by pre-welding, or by gluing with a biocompatible adhesive) to provide a fixed, pre-ordained spaced apart relationship between the facet surface elements 34. The preordained, fixed position of and the spacing between the facet joint structure elements 34 can vary, e.g., among prostheses 26 intended for children and adults, as well as for male and females. The physician can also select the desired position of the facet joint structure elements 34 based upon prior analysis of the morphology of the targeted joint using, for example, plain film x-ray, fluoroscopic x-ray, or MRI or CT scanning.

The facet joint structure elements 28 can be located at or near the typical anatomic position of the caudal portion of the facet joint, which would be generally aligned with the fixation element 32 (as FIG. 7 shows in connection with another embodiment, which will be described later). Alternatively, if desired, and as shown in FIG. 3, the facet joint structure elements 34 can be fixed within a range of pre-ordained locations medial of the typical anatomic location. Still alternatively, and as shown in FIG. 4, one or both of the facet joint structure elements 34 can be fixed within a range of preordained positions lateral of the typical anatomic position.

Figure 5:
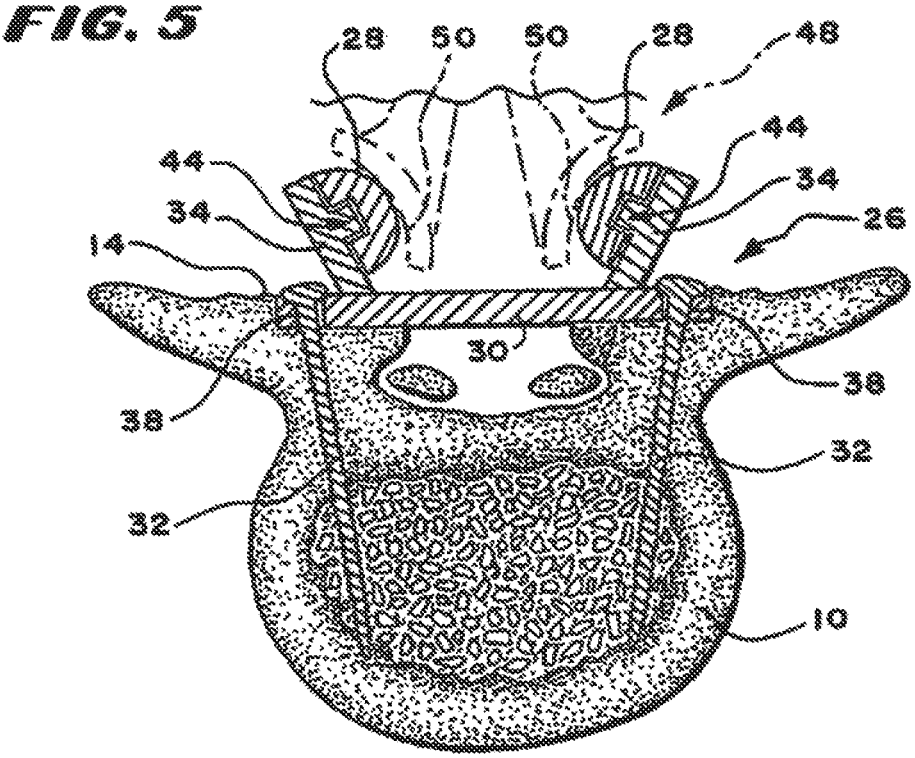
FIG. 5 is a superior section view of a vertebral body, showing the fixation of a caudal prosthesis of the type shown in FIG. 3, the artificial facet joint structure elements in FIG. 5 having a generally ball-shaped geometry and being shown in positions medial of the typical anatomic position of the superior half of the facet joint.
Figure 6:
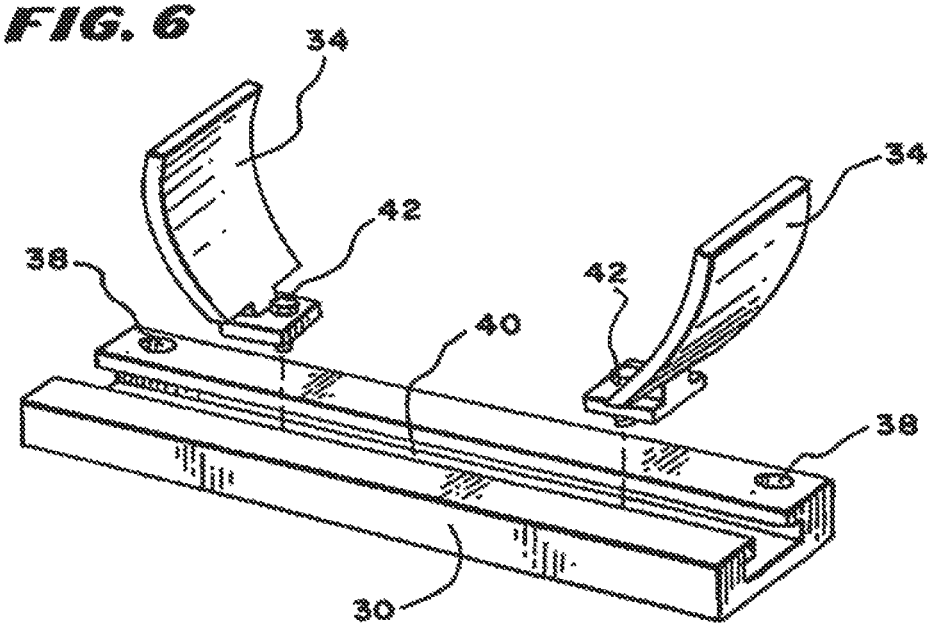
FIG. 6 is an enlarged perspective view of a caudal prosthesis of the type shown in FIG. 3, showing a mechanism that allows movement of the artificial facet joint structure elements to adjust their relative spaced-apart positions on the prosthesis.

Alternatively, one or both of the facet joint structure elements 34 can be carried by the bar element 30 for relative movement, e.g., in a track 40 extending in the bar element (see FIG. 5). In this arrangement, the position of the movable facet joint structure element(s) 34 can be infinitely varied during surgery to match the particular anatomy of the facet joint or joints being replaced. In this arrangement, a set screw 42 or the like can secure the position of the movable facet joint structure element 34 along the track 40.

Whether one or more of the facet joint structure elements 34 are fixed or movable relative to the bar element 30, the prosthesis 26 can accommodate a variety of different symmetric or asymmetric anatomic situations, e.g., where the caudal portion of the facet joint on one side of a vertebral body 10 are differently spaced from those on the other side of the same body 10. The prosthesis 26 can include adjustable facet joint structure elements 34, or, alternatively, it can be pre-formed with various fixed relative positions of left and right facet joint structure elements 34, either symmetric and asymmetric; e.g., left and right typical; or left and right medial; or left and right lateral; or left medial and right lateral, or combinations thereof.

The invention thereby makes it possible for a surgeon to install a "custom" implant during the surgical procedure.

The facet joint structure elements 34 may be made of a biocompatible polymer (e.g., polyethylene or rubber), or a biocompatible ceramic, or bony in-growth surface, or sintered glass, or artificial bone, or a combination thereof. The material is selected to provide glide and cushioning ability for potential contacting components. Desirably, these surface materials are, for strength, backed by a biocompatible metal (e.g., titanium, titanium alloys, chrome cobalt, or surgical steel).

The geometry of the caudal facet joint structure elements 34 can also vary, depending on the geometry of the matching cephalad portions of a facet joint or facet joint replacement. As shown in FIGS. 3 and 4, the caudal facet joint structure elements 34 may be generally concave or cup-shaped, to thereby articulate with generally convex or ball-shaped facet joint structures of the cephalad portion of the facet joint or facet joint replacement. Alternatively, as shown in FIG. 5, the caudal facet joint structure elements 34 may be generally convex or ball-shaped, to thereby articulate with generally concave or cup-shaped facet joint structure of the cephalad portion of the facet joint replacement The ball-shaped elements and the cup-shaped elements can have various diameters and arcs of curvature. Preferably, the ball-shaped element is elliptical or round.

The cup-shaped elements may be any appropriate shape including, but not limited to, rectangular, disc shaped, trough shaped, or cup shaped. The cup-shaped element is desirably sized larger than the articulating ball-shaped half of the facet joint, to allow for motion of the joint.

Regardless of geometry, the facet joint structure elements 34 can be fixedly attached or removably attached, e.g., by Morse tapers 44 (see FIG. 5), or screws, slots, and the like.

In an alternative arrangement (see FIG. 7), the bar element 30 and facet joint structure elements 34 form a preformed unit, and the fixation elements 34 comprise stems 46 secured to the vertebral body 10. The stems 46 are secured by insertion into the pedicles 14 (e.g., by screwing or tapping). In FIG. 7, there are two stems 46 inserted, respectively, into the left and right pedicles 14.

In this arrangement, the bar element 30 and facet joint structure elements 34 are desirably secured as a preformed unit with compressive forces or friction to the stems 46, e.g., by Morse tapers 44, to thereby enable their removal and replacement as a unit. Alternatively, the bar element 30 and facet joint structure elements 34 can be fixedly attached as a unit to the stem 46, e.g., by adhesive, screw, nail, or any means known in the art.

As FIGS. 7 and 8 show, the geometry of the caudal facet joint structure elements 34 on the bar element 30 attached to the stems 46 can vary, as previously described, depending on the geometry of the matching cephalad portions of a facet joint or facet joint replacement. As shown in FIG. 7, the caudal facet joint structure elements 34 may be generally concave or cup-shaped, to thereby articulate with generally convex or ball-shaped facet joint structure of the cephalad portions of the facet joint or facet joint replacement. Alternatively, as shown in FIG. 8, the caudal facet joint structure elements may be generally convex or ball-shaped, to thereby articulate with generally concave or cup-shaped facet surfaces of the cephalad portions of the facet joint replacement.

The caudal prosthesis 26 for the superior half of the facet joint replacement described above may be used as a replacement for the caudal portions of one or more of facet joints at any facet joint at any level of the spine. In the preferred embodiment, the prosthesis 26 is used to replace the caudal portion of one or more facet joints. The prosthesis 26 is designed such that it has the appropriate cephalad and caudad directions as well as the appropriate medial/lateral angulation for the given level of the spine where the implant occurs.

In further embodiments, one or more surfaces of a prosthesis 26 may be covered with various coatings such as antimicrobial, antithrombotic, and osteoinductive agents, or a combination thereof. See, e.g., U.S. Pat. No. 5,866,113, which is incorporated herein by reference. These agents may further be carried in a biodegradable carrier material with which the pores of the stem and/or cup member of certain embodiments may be impregnated. See, e.g., U.S. Pat. No. 5,947,893, which is also incorporated herein by reference.

In still further embodiments of the present invention, the prosthesis 26 may be attached to strengthened or fortified bone. Vertebrae may be strengthened prior to or during fixation of the prostheses using the methods, e.g., described in U.S. Pat. No. 5,827,289, which is incorporated herein by reference. This type of bone strengthening is particularly suggested for osteoporotic patients who wish to have facet replacement.

B. Surgical Method for Facet Replacement Using the Caudal Prosthesis

A surgical procedure removes and replaces the caudal portion of a facet joint with the caudal prosthesis 26 described above.

In one embodiment, the surgical procedure comprises exposing the spinous process, lamina, and facet joints at a desired level of the spine using any method common to those of skill in the medical arts. Prominent bone of the caudal portion of the natural facet joint natural, e.g., the superior articular process 22 and its supporting bone, may rongeured using any means common in the field. The caudal portion of the natural facet joint may also be trimmed to decompress the adjacent nerve root. A reamer or any other instrument that is useful for grinding or scraping bone, may be used to ream the caudal portion of the facet joint into the pedicle, to reach the geometry shown in FIG. 3, which is suitable for receiving the caudal prosthesis 26.

Figure 9:
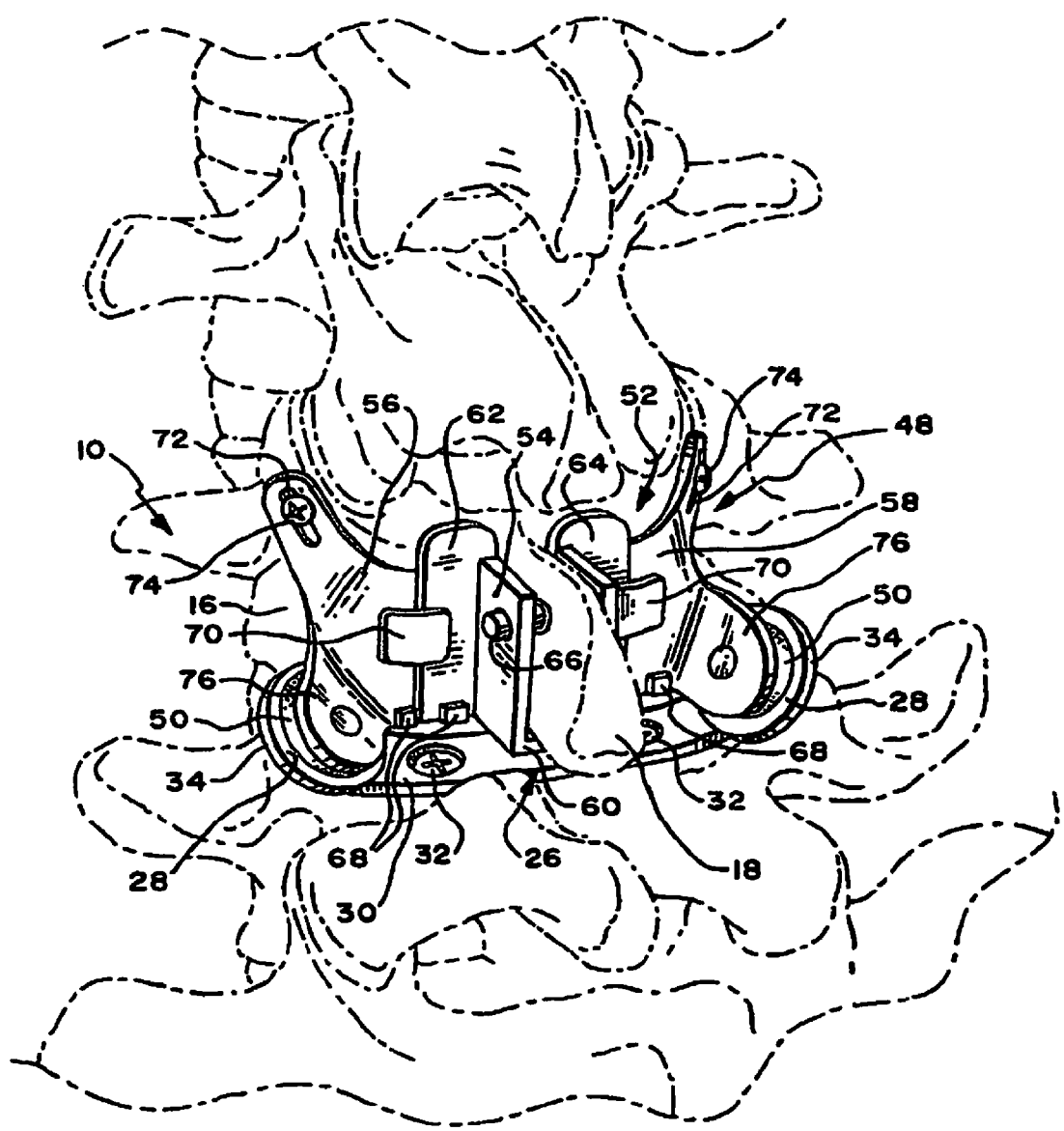
FIG. 9 is a perspective posterior view of the spinal column, showing the fixation of a cephalad prosthesis across the lamina of a vertebral body, the cephalad prosthesis carrying facet joint structure elements that create artificial facet surfaces for the inferior half of a facet joint replacement, FIG. 9 also showing the fixation of a caudal prosthesis of the type shown in FIG. 3 carrying facet joint structure elements that create artificial facet surfaces for the superior half of a facet joint replacement, the two prosthesis together created a total facet replacement system.

The prosthesis can then directly screwed or tapped into the vertebral body 10 using pedicle screws or other fixation elements. Because the caudal portion of the natural facet joint has been removed, the artificial facet joint structure of the caudal prosthesis 26 can be installed in a desired position and orientation, free of anatomic constraints imposed by the preexisting articular configuration of the caudal portion of the natural facet joint. Furthermore, the artificial facet joint structure of the caudal prosthesis 26 can comprise an artificial articular configuration that is unlike the preexisting articular configuration of the natural facet surface (which is removed), so that a desired articulation or bony anatomy can be totally restored. Furthermore, decompression of the adjacent nerve root can be maintained, eliminating pain at the same time a desired anatomy is restored Further details of surgical procedures suitable for installing the prosthesis 26 are described in co-pending U.S. patent application Ser. No. 09/693,272, filed Oct. 20, 2000, and entitled "Facet Arthroplasty Devices and Methods," which is incorporated herein by reference III. Cephaled Prosthesis A. Structure FIG. 9 shows a cephalad facet joint replacement prosthesis 48 that embodies features of the invention. The prosthesis 48 is designated "cephalad" because it provides an artificial facet joint structure element 50 for the inferior half of a facet joint replacement. The cephalad prosthesis 48 allows for the removal and replacement of injured, diseased and/or deteriorating natural inferior articular surfaces and supporting boney structure on the vertebral body above the facet joint, to provide improved support for the spinal column.

The artificial facet joint structure 50 articulates with the superior half of the facet joint, which itself can comprise the natural caudal portions of the facet joint (i.e., the natural superior articular surfaces and supporting boney structure on the vertebral body below the facet joint), or an artificial facet joint structure formed by a caudal joint replacement prosthesis 28.

In FIG. 9, the superior half of the facet joint replacement comprises the caudal facet joint structure 28 of the prosthesis 26 of the general type shown in FIGS. 3 and 4. In FIG. 9, the caudal facet joint structure 28 comprise cup-shaped caudal facet joint structure elements 34, which, in FIG. 9, are mutually located on the bar element 30 in positions lateral of the typical anatomic location. As shown in FIGS. 3 and 4, the relative position of the cup-shaped caudal facet joint structure elements 34 can vary among the typical anatomic position, a position medial of this position, and a position lateral of this position, as has already been explained. The cephalad facet joint structure elements 50 are positioned to align with the caudal facet joint structure elements 34.

The cephalad prosthesis 48 shown in FIG. 9 desirably spans the lamina 16 from the left side of a vertebral body 10 to the right side of the vertebral body 10. The cephalad prosthesis 48 thereby makes possible the removal and replacement of injured, diseased and/or deteriorating components along the cephalad portions of both left and right facet joints, to provide improved support for the spinal column. The cephalad prosthesis 48 allows for replacement of diseased and deteriorating inferior portions of the vertebra and partial replacement of lamina, which may be pressing on the spinal nerves, to relieve pain. The cephalad prosthesis 48 creates artificial facet joint structure elements 50 for the inferior half of facet joints in the spine, which provide improved support for the spinal column.

Because the cephalad portion of the natural facet joint is removed, the artificial facet joint structure element 50 of the cephalad prosthesis 48 can be installed in a desired position and orientation, free of anatomic constraints imposed by the preexisting articular configuration of the cephalad portion of the natural facet joint. Furthermore, the artificial facet joint structure element 50 of the cephalad prosthesis 48 can comprise an artificial articular configuration that is unlike the preexisting articular configuration of the natural facet surface (which is removed), so that a desired articulation or bony anatomy can be totally restored. Furthermore, decompression of the adjacent nerve root can be maintained, eliminating pain at the same time a desired anatomy is restored.

As FIG. 9 shows, the caudal prosthesis 26, e.g., as described above, may also be installed with the cephalad prosthesis 48, to replace both the caudal and cephalad portions of the natural facet joint, after both caudal and cephalad portions of the natural facet joint are surgically removed. Together, the caudal and cephalad prostheses 26 and 48 form a total facet replacement system 52.

Because the system 52 entails removal of both the caudal and cephalad portions of the natural facet joints, the placement of the total facet replacement system 52 is not necessarily constrained by normal anatomic considerations. To attain desired alignment and load conditions, the artificial facet joint structures 28 and 48 can be positioned along, medial of, or lateral of the normal anatomic locations of the facet joints. Likewise, the facet joint structures 28 and 48 can be positioned at or slightly superior or slightly inferior to the normal anatomic location of the facet joints.

The system 52 can provide a succession of entirely artificial facet joints along a length of the spinal column. Alternatively, just the inferior half one or more facet joints, or just the superior half of one or more facet joints, may be replaced. The inferior and/or superior halves of facet joints may be replaced on one side of a given vertebra (unilateral), on the both sides of a given vertebra (bilateral), or a combination of each along a length of the spinal column. At the same time a desired bone anatomy is restored, decompression of the adjacent nerve root can be maintained to eliminate pain.

In the embodiment shown in FIG. 9, the cephalad prosthesis 48 comprises three separate components—a central component 54 and arm components 56 and 58 (left and right).

The central component 54 may be variously constructed. In the illustrated embodiment, the central component 54 comprises a spinous process chimney 60 and left and right lamina plates 62 and 64. The spinous process chimney 60 functions to surround and stabilize the posterior aspect of the spinous process 18. If desired, the spinous process 18 may be fixed between interior walls of the spinous process chimney 60 with a trans-spinous process screw 66.

The left and right lamina plates 62 and 64 contact the lamina 16, to aid fixation of the central component 54 to the vertebral body 10. The plates 62 and 64 can be secured to the lamina 16 by various ways, e.g., poly(methylmethacrylate) bone cement, hydroxyapatite, screws, nails, bolts, anchors, break-away screws to facilitate any future removal of the prosthesis, or a combination thereof, or any other means known in the art. Lamina hooks 68 are also desirably used to push against the lamina 16, thereby adding additional stability.

The left and right arm components 56 and 58 attach by a coupling to medial sides of the left and right lamina plates 62 and 64. The coupling junction 70 between the arm components 56 and 58 and the lamina plates 62 and 64 may take a number of different forms, including, e.g., a slotted joint between the plate 62/64 and the respective arm 56/58. Alternatively, a screw attachment, a hook attachment, or a snap-fit attachment can be used The left and right arm components 56 and 58 each include a superior opening 72. Each opening 72 accommodates passage of a fixation element 74. In FIG. 9, the fixation elements 74 take the form of bilateral pedicle screws or nails, but other forms of fixation can be used.

The fixation elements 74 secure the superior portions of the left and right arm components 56 and 58, respectively, to the left and right pedicles 14 of the vertebral body 10. One or both openings 72 could be elongated, either along the superior-inferior axis of the vertebral body 10 or transverse this axis, to allow for varying orientations and/or sizes of the pedicle screw Passage of the pedicle screws through the openings 72 provides straightforward and flexible fixation of the left and right arm components 56 and 58 to the vertebral body. Lamina hooks 68 are also desirably used to push against the lamina 16, thereby adding additional stability.

The left and right arm components 56 and 58 also each includes a depending cephalad facet joint structure element 76. The facet joint structure elements 76 are sized and located for articulation with a natural caudal portion of the facet joint or an artificial caudal facet joint structure element.

The relative position and geometry of the cephalad facet joint structure elements 76 can of course vary, depending on the relative positions and geometry of the matching natural caudal portion of the facet joint or an artificial caudal facet joint structure element. As shown in FIG. 9, the cephalad facet joint structure elements 76 may be generally convex or ball-shaped, to thereby articulate with generally concave or cup-shaped facet joint structure elements 34 of the caudal prosthesis. This articulation is also shown in phantom lines in FIGS. 3 and 4, with the facet joint structure elements 34 and 76 arranged at alternative, different anatomic positions.

Alternatively, as shown in phantom lines in FIG. 5, the cephalad facet joint structure elements 76 may be generally concave or cup-shaped, to thereby articulate with generally convex or ball-shaped facet joint structure elements 34 of the caudal prosthesis As before explained, the ball-shaped joint structure elements and the cup-shaped joint structure elements can have various diameters and arcs of curvature.

Regardless of geometry, as with the caudal facet joint structure elements 34, the cephalad facet joint structure elements 76 can be fixedly attached to the respective arm component 56 and 58. Alternatively, the cephalad facet joint structure elements 76 can be removably attached to the respective arm component 56 and 58, e.g., by Morse tapers 44, or screws, slots, and the like.

Regardless of geometry, the cephalad facet joint structure elements 76 may be made of a biocompatible polymer (e.g., polyethylene or rubber), or a biocompatible ceramic, or bony in-growth surface, or sintered glass, or artificial bone, or a combinations thereof. Desirably, these surface materials are backed by a biocompatible metal (e.g., titanium, titanium alloys, chrome cobalt, or surgical steel).

The central component 54 and the left and right arm components 62 may be made of material commonly used in the prosthetic arts including, but not limited to, polyethylene, rubber, titanium, chrome cobalt, surgical steel, bony in-growth sintering, sintered glass, artificial bone, ceramics, or a combination thereof.

In further embodiments, one or more surfaces of the cephalad prosthesis 48 may be covered with various coatings such as antimicrobial, antithrombotic, and osteoinductive agents, or a combination thereof. See, e.g., U.S. Pat. No. 5,866,113, which is incorporated herein by reference. These agents may further be carried in a biodegradable carrier material with which the pores of the base member and/or any screws, bolts, or nails of certain embodiments may be impregnated. See, e.g., U.S. Pat. No. 5,947,893, which is incorporated herein by reference.

In other arrangements, the cephalad prosthesis 48 may be attached to strengthened or fortified bone. Vertebrae may be strengthened prior to or during fixation of the prosthesis using the methods described, e.g., in U.S. Pat. No. 5,827,289, which is incorporated herein by reference. This type of bone strengthening is particularly suggested for osteoporotic patients who wish to have facet replacement.

B. Surgical Method for Lamina/Facet Replacement Using the Cephalad Prosthesis

A surgical procedure removes and replaces the inferior lamina 16 and the cephalad portion of the facet joint (e.g., the articulated inferior processes 24 and its supporting bone of the targeted vertebral body 10) with the cephalad prosthesis 48 as described above.

In one embodiment, the surgical procedure exposes the spinous process, lamina, and facet joints at a desired level of the spine using any method common to those of skill in the medical arts. The cephalad portion of the facet joint is cut at or near a selected resection line. Most of the lamina 16 is desirably preserved, as is the facet joint capsule, which may be opened and folded back. The facet joint capsule may be cut perpendicular to its direction. The cephalad portion of the facet joint may then be retracted from the caudal portion. Once the facet joint 620 is separated, the cut inferior bone of the upper joint (e.g., the cut inferior portion of the L4 vertebra in the L4-L5 joint) may be removed. Alternatively, it may be possible to remove the cut inferior bone while simultaneously separating the facet joint.

The caudal prosthesis 26 can also be installed as previously described, either before of after the inferior bone is removed or even cut.

The cephalad prosthesis 48 as described above is placed over the spinous process 18 over the lamina 16. The cephalad prosthesis 48 is attached as above described to the lamina 16 and to each pedicle. The cephalad prosthesis 48 may also be further attached to the spinous process 18 with a trans-spinous-process screw 66 to provide additional stability, as also previously described.

Further details of surgical procedures suitable for installing the prosthesis 48 are described in co-pending U.S. patent application Ser. No. 09/693,272, filed Oct. 20, 2000, and entitled "Facet Arthroplasty Devices and Methods," which is incorporated herein by reference.

The size and shape of any prosthesis disclosed herein are desirably selected by the physician, taking into account the morphology and geometry of the site to be treated. The shape of the joint, the bones and soft tissues involved, and the local structures that could be harmed if move inappropriately, are generally understood by medical professionals using textbooks of human anatomy along with their knowledge of the site and its disease and/or injury. The physician is also desirably able to select the desired shape and size of the prosthesis and its placement in and/or around the joint. based upon prior analysis of the morphology of the targeted joint using, for example, plain film x-ray, fluoroscopic x-ray, or MRI or CT scanning. The shape, size and placement are desirably selected to optimize the strength and ultimate bonding of the prosthesis to the surrounding bone and/or tissue of the joint.

Other embodiments and uses of the invention will be apparent to those skilled in the art from consideration of the specification and practice of the invention disclosed herein. All documents referenced herein are specifically and entirely incorporated by reference. The specification and examples should be considered exemplary only with the true scope and spirit of the invention indicated by the following claims. As will be easily understood by those of ordinary skill in the art, variations and modifications of each of the disclosed embodiments can be easily made within the scope of this invention as defined by the following claims.

What is claimed is:

1. A prosthetic system comprising:
   a bar member comprising a left side region and a right side region, wherein the bar member comprises a track;
   a first fixation area on the left side region;
   a second fixation area on the right side region;
   a first fixation element received in the first fixation area;
   a second fixation element received in the second fixation area;
   a first facet joint structure element positioned nearer to the first fixation area than the second fixation area; and
   a second facet joint structure element positioned nearer to the second fixation area than the first fixation area, wherein the first facet joint structure and the second facet joint structure are each received within the track.

2. The system of claim 1, wherein the first facet joint structure element is articulatable.

3. The system of claim 1, wherein the bar element comprises a fixed length.

4. The system of claim 1, wherein the bar element comprises a sliding joint.

5. The system of claim 1, wherein the first facet joint structure is fixed to the bar member via welding or an adhesive.

6. The system of claim 1, wherein the track is positioned along a midline of the bar member.

7. The system of claim 1, wherein the distance of separation between the first facet joint structure and the second facet joint structure can vary.

8. The system of claim 1, wherein a first set screw secures the first facet joint structure along the bar member and a second set screw secures the second facet joint structure along the bar member.

9. The system of claim 1, wherein the first facet joint structure comprises a concave surface and the second facet joint structure comprises a concave surface.

10. The system of claim 9, wherein the first concave surface and the second concave surface face each other.

11. The system of claim 1, wherein the first facet joint structure comprises a convex surface and the second facet joint structure comprises a convex surface.

12. A prosthetic system comprising:
- a bar member comprising a left side region and a right side region, wherein the bar member comprises a track;
- a first fixation element received through the left side region;
- a second fixation element received through the right side region;
- a first facet joint structure element positioned nearer to a first fixation area than a second fixation area; and
- a second facet joint structure element positioned nearer to the second fixation area than the first fixation area, wherein the first facet joint structure element is positioned within the track and the second facet joint structure element is positioned within the track, wherein the first facet joint structure element is moveable along the track relative to the second facet joint structure,
- wherein a distance of separation between the first facet joint structure and the second facet joint structure is adjustable.

13. The system of claim 12, wherein the bar member has a fixed length.

14. The system of claim 12, wherein the bar member has an adjustable length.

15. The system of claim 14, wherein the bar member has a sliding joint.

16. The system of claim 12, wherein first facet joint structure comprises a first convex surface and the second facet joint structure element comprises a second convex surface that faces the first convex surface.

* * * * *